United States Patent
Ley et al.

(10) Patent No.: US 6,416,538 B1
(45) Date of Patent: *Jul. 9, 2002

(54) STENT CONFIGURATIONS

(75) Inventors: Timothy J. Ley, Shoreview; Graig L. Kveen, Maple Grove; Timothy G. J. Ehr, Elk River; Brian J. Brown, Hanover; David L. Friesen, Brooklyn Park, all of MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/316,827

(22) Filed: May 21, 1999

Related U.S. Application Data (63) Continuation of application No. 08/947,620, filed on Oct. 9, 1997, now Pat. No. 6,013,091.

(51) Int. Cl.$^7$ .................................................. A61F 2/06
(52) U.S. Cl. ..................................................... 623/1.15
(58) Field of Search ................................ 606/191, 198; 623/1.1, 1.15, 1.17

(56) References Cited

U.S. PATENT DOCUMENTS

| | | |
|---|---|---|
| 5,449,373 A | 9/1995 | Pinchasik et al. |
| 5,591,197 A | 1/1997 | Orth et al. |
| 5,603,721 A | 2/1997 | Lau et al. |
| 5,630,829 A | 5/1997 | Lauterjung |
| 5,653,727 A | 8/1997 | Wiktor |
| 5,669,932 A | 9/1997 | Fischell et al. |
| 5,695,516 A | 12/1997 | Fischell et al. |
| 5,697,971 A | 12/1997 | Fischell et al. |
| 5,716,396 A | 2/1998 | Williams, Jr. .................. 623/1 |
| 5,718,713 A | 2/1998 | Frantzen .................... 606/198 |
| 5,741,327 A * | 4/1998 | Frantzen .................... 606/191 |
| 5,755,776 A | 5/1998 | Al-Saadon .................... 623/1 |
| 5,810,872 A | 9/1998 | Kanesaka et al. ........... 606/198 |
| 5,935,162 A * | 8/1999 | Dang ........................ 623/1.15 |

FOREIGN PATENT DOCUMENTS

| | | |
|---|---|---|
| DE | 296 15 969 U1 | 12/1996 |
| DE | 297 01 758 U1 | 5/1997 |
| DE | 297 02 671 U1 | 5/1997 |
| DE | 297 08 689 U1 | 8/1997 |
| DE | 297 08 879 U1 | 9/1997 |
| DE | 297 16 476 | 2/1998 |
| DE | 298 05 761 | 9/1998 |
| JP | 10-155915 | 6/1998 |
| JP | 10-165513 | 6/1998 |
| JP | 10-201856 | 8/1998 |
| WO | WO 95/09584 | 4/1995 |
| WO | WO 96/03092 A1 | 2/1996 |
| WO | WO 97/04721 | 2/1997 |
| WO | 97/25937 | 7/1997 |
| WO | WO 97/26840 | 7/1997 |
| WO | WO 97/32543 | 9/1997 |
| WO | WO 97/32544 | 9/1997 |
| WO | WO 97/33534 | 9/1997 |
| WO | 98/18405 | 5/1998 |
| WO | 98/18406 | 5/1998 |

* cited by examiner

*Primary Examiner*—Kevin T. Truong
(74) *Attorney, Agent, or Firm*—Vidas, Arrett & Steinkraus

(57) ABSTRACT

Improved stent configurations exhibiting limited recoil, resistance to compression and improved longitudinal flexibility.

19 Claims, 12 Drawing Sheets

STENT CONFIGURATIONS

CROSS-REFERENCE TO RELATED APPLICATIONS

This application is a Continuation of U.S. application Ser. No. 08/947,620 filed Oct. 9, 1997, now U.S. Pat. No. 6,013,091 the contents of which are incorporated herein in their entirety by reference.

BACKGROUND OF THE INVENTION

1. Field of the Invention

This invention relates to stents of improved configuration.

2. Brief Description of the Prior Art

Stents are radially expandable endoprosthesis which are typically intravascular implants capable of being implanted transluminally and enlarged radially after being introduced percutaneously. They have also been implanted in urinary tracts and bile ducts. They are used to reinforce body vessels and to prevent restenosis following angioplasty in the vascular system. They may be self-expanding or expanded by an internal radial force, such as when mounted on a balloon.

In the past, stents have been generally tubular but have been composed of many configurations and have been made of many materials, including metals and plastic. Ordinary metals such as stainless steel have been used as have shape memory metals such as Nitinol and the like. Stents have also been made of biodegradable plastic materials. Such stents have been formed from wire, tube stock, etc.

SUMMARY OF THE INVENTION

This invention provides new configurations of the cells making up stents which may be adapted to all of the various types of prior art stents described above and/or known previously in the art. There are numerous advantages to the new configurations. The configurations of the invention limit recoil and add resistance to compression for an expanded stent, among other things. Other configurations than cylindrical are contemplated, e.g., square, triangular octagonal, etc. The stents of this invention are longitudinally flexible and expandable.

DETAILED DESCRIPTION OF THE PREFERRED EMBODIMENTS

Figure 1:
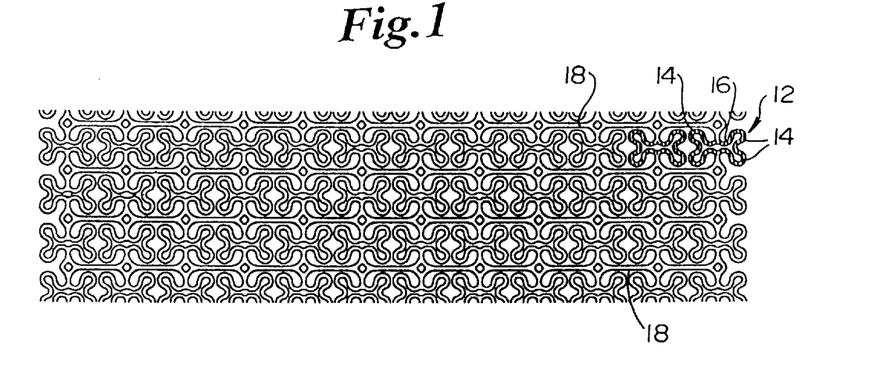
FIG. 1 is a flat plan view of an embodiment of the stent configuration of the invention in the unexpanded condition.
Figure 1A:
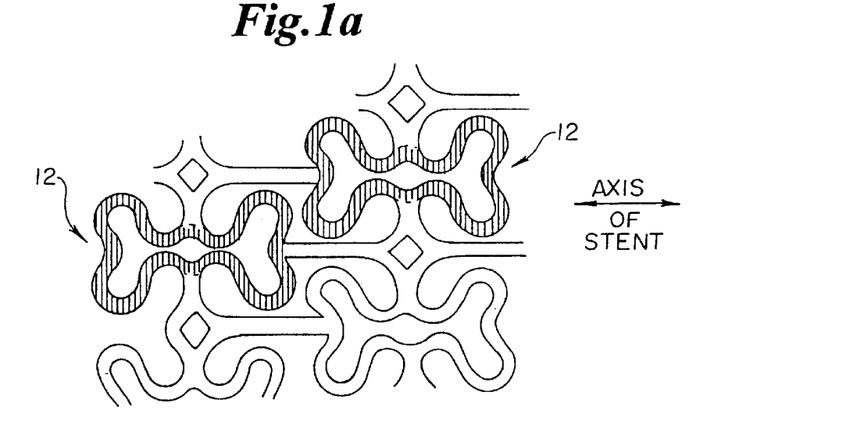
FIG. 1a is a fragmentary plan similar to FIG. 1 showing a staggered arrangement of the cells making up a stent.
Figure 1B:
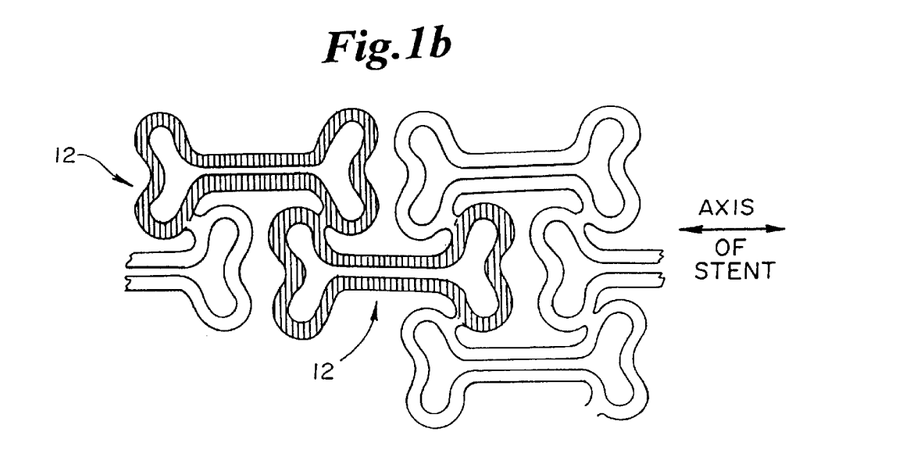
FIGS. 1b and 1c show cells similar to FIG. 1 and 1a in different arrangements and with differing interconnection.
Figure 1C:
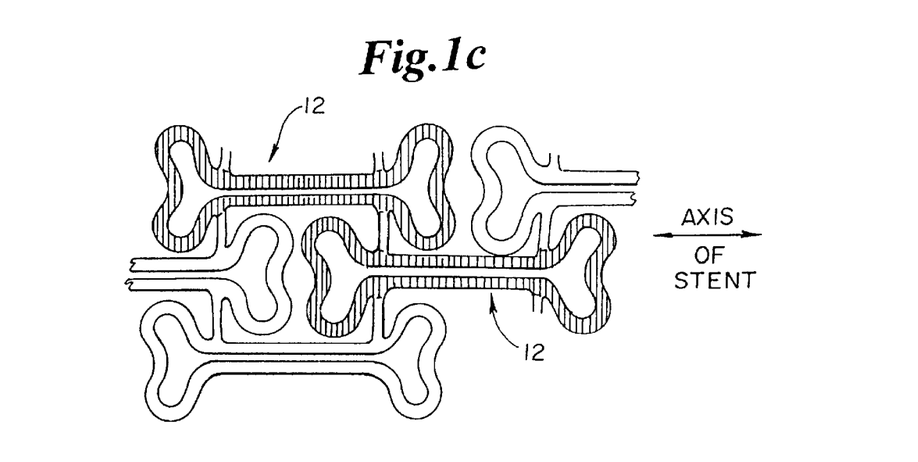
Figures 2, 3:
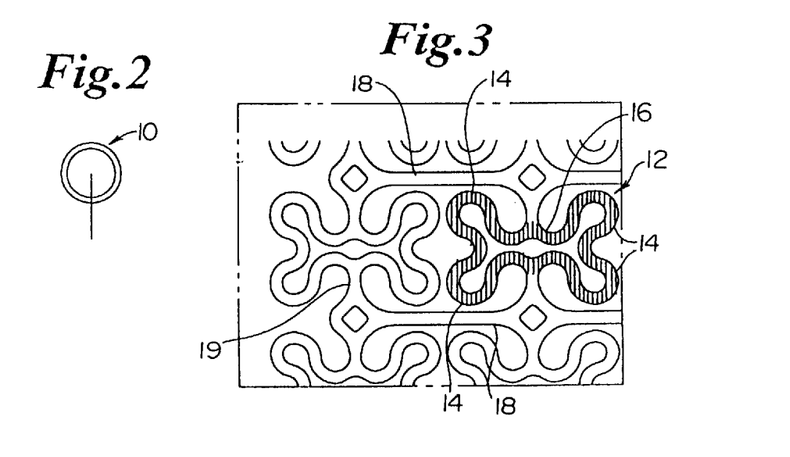
FIG. 2 is an end view of a stent of FIG. 1 according to the invention in its normal tubular unexpanded condition.
FIG. 3 is a detail view of a portion of FIG. 1, as indicated.
Figure 4:
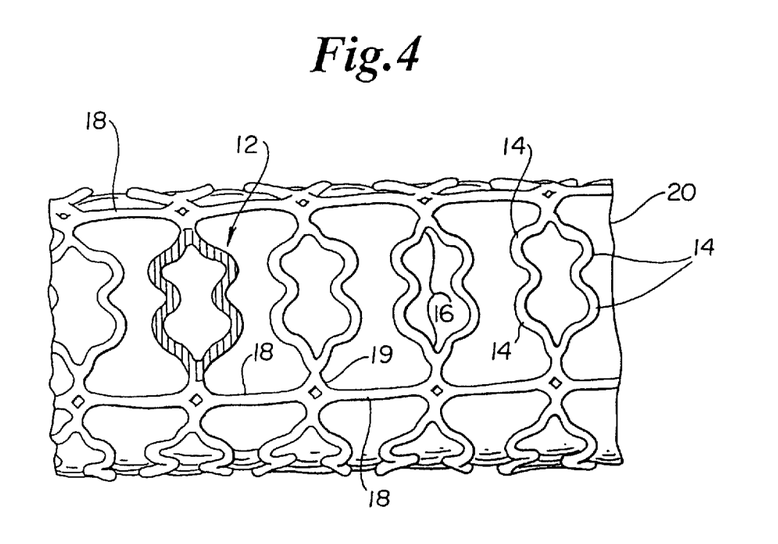
FIG. 4 is a view of the stent of FIGS. 1 and 2 expanded on a balloon.

A preferred embodiment of a generally cylindrical stent 10 according to the invention is illustrated in FIGS. 1–4. It comprises a metal tube as shown in FIGS. 2 and 4, such as nitinol or stainless steel preferably, which has been etched or preferably laser cut to the configuration shown in the flat plan view of FIG. 1. An enlarged detail of FIG. 1 is shown in FIG. 3. The configuration is made up of a series of curvilinear expansion cell elements generally indicated at 12 (see darkened example in FIG. 3 for clarity) having relatively wide end portions 14 joined by relatively narrow center portions 16. Cells 12 are arranged longitudinally as shown in FIG. 1 end to end with respect to the longitudinal axis of the stent 10 and in substantially parallel rows as also shown in FIG. 1. A plurality of longitudinally extending elongate support members 18 are included, one each being disposed between adjacent rows of cells 12. Also, a plurality of circumferentially extending support members 19, preferably substantially normal to support members 18 are also positioned between the rows of cells 12 to intersect portions of the support members 18 and to interconnect them to the narrow center portions 16 of cells 12. As can be seen in FIG. 1a, cells 12 may also be arranged in a staggered arrangement. FIGS. 1b and 1c demonstrate different arrangements and interconnections for cells 12.

When the stent is expanded, as shown in FIG. 4, on a balloon 20 the cells 12 take on a new configuration as shown, the members making up the stent being indicated by the same numbers as used in FIG. 1 and FIG. 3. Again, one cell is shown darkened for clarity.

Figure 5:
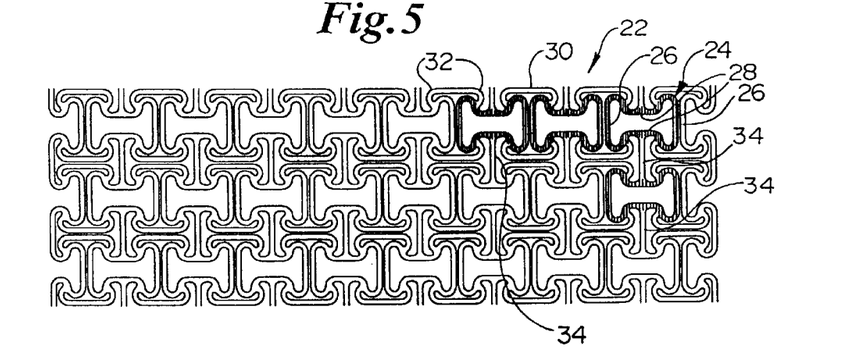
FIG. 5 is another stent embodiment of the invention similar in view to FIG. 1 showing the flat plan of the stent in the unexpanded configuration.
Figure 6:
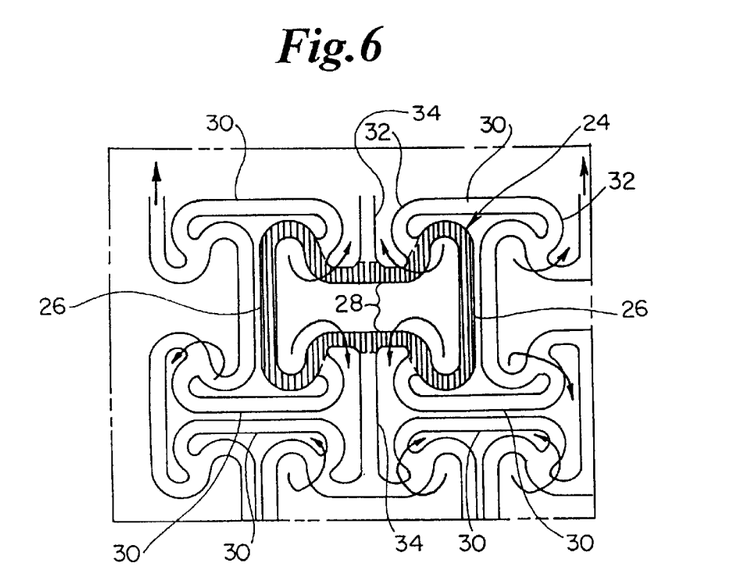
FIG. 6 is a detail view of a portion of FIG. 5, as indicated.
Figure 7:
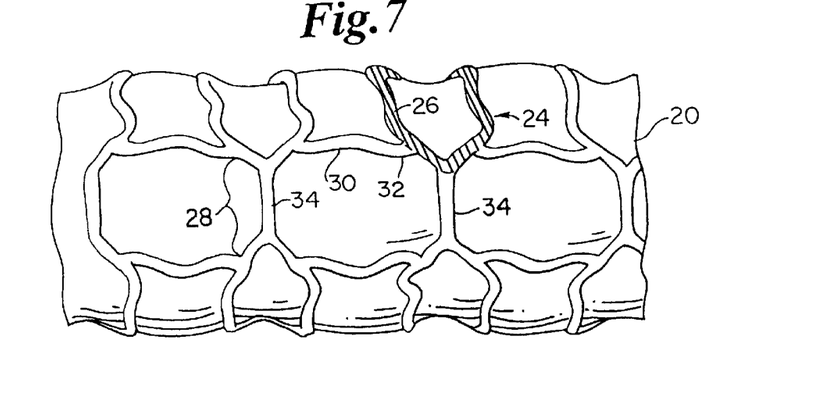
FIG. 7 is a showing of the stent of FIG. 4 expanded on a balloon.

Referring now to FIGS. 5–7, another stent embodiment generally indicated at 22 of the invention is shown. In this embodiment, as seen in FIGS. 5 and 6, expansion cells 24, best seen in the detail of FIG. 6 and indicated by darkened portion, have relatively wide end portions 26, best seen in FIG. 6, and narrow center portions 28 and are arranged end to end in longitudinal rows as described with respect to the first embodiment. Adjacent end portions 26 are interconnected by pairs of longitudinal support members in the form of segments 30 which have curved end portions 32. Circumferential extending segments 34 extend between rows of cells 24 to interconnect the narrow center portions 28.

Upon radial expansion of the stent, as on a balloon 20 for example, its configuration changes by deformation force in the directions shown by the arrows in FIG. 6 to that configuration shown in FIG. 7. The elements indicated in FIG. 7 are identified by the same numbers indicated for similar elements in FIGS. 5 and 6.

Figure 20:
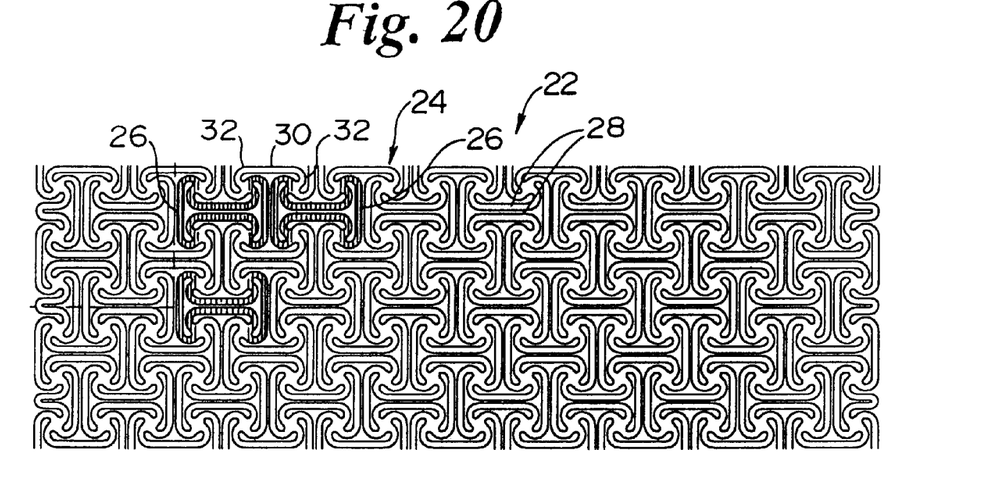
FIG. 20 is a flat plan view similar to FIGS. 1, 5, 8, 11, 15 and 18 showing yet another stent embodiment in the unexpanded condition.
Figure 21:
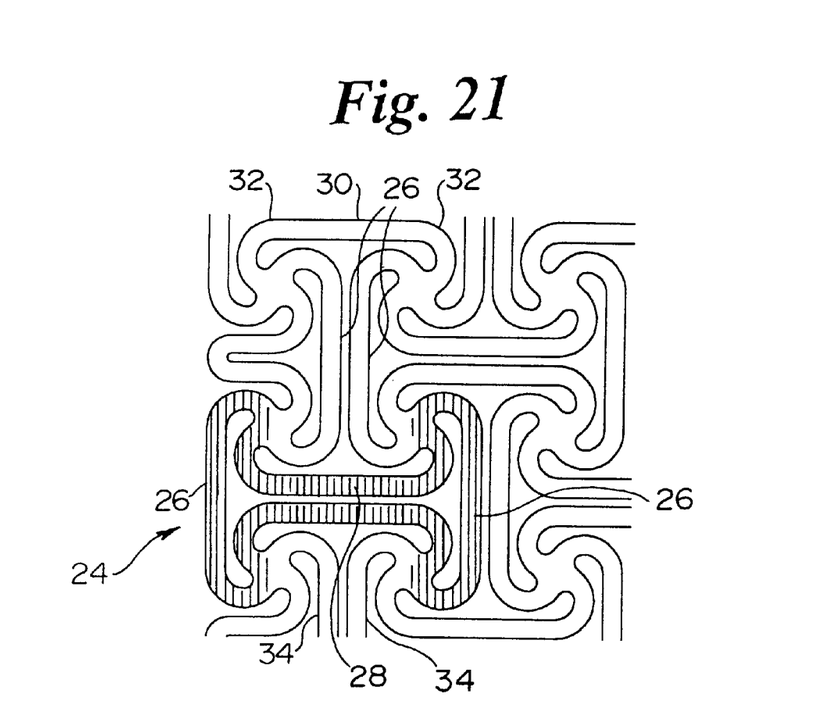
FIG. 21 is a detail view of a portion of FIG. 20.

FIGS. 20 and 21 show a configuration somewhat similar to that of FIGS. 5–7 but without interconnecting elements 28.

Figure 8:
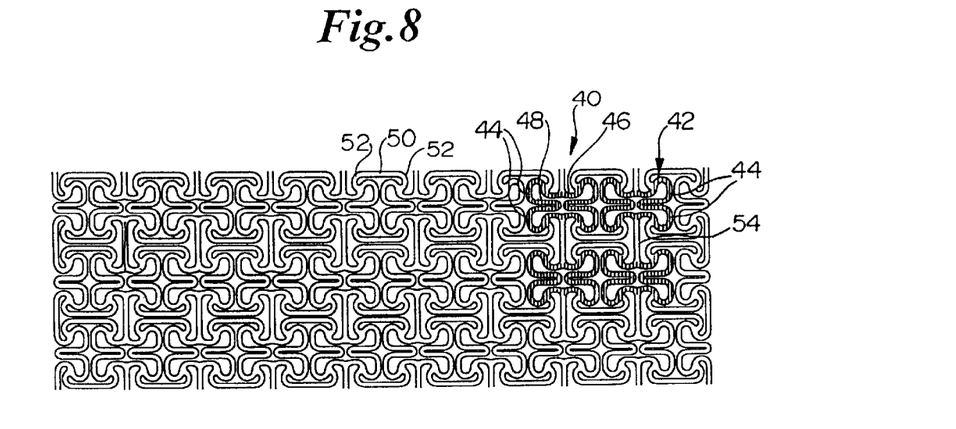
FIG. 8 is a flat plan similar to FIGS. 1 and 5 showing another stent embodiment in the unexpanded condition.
Figure 8A:
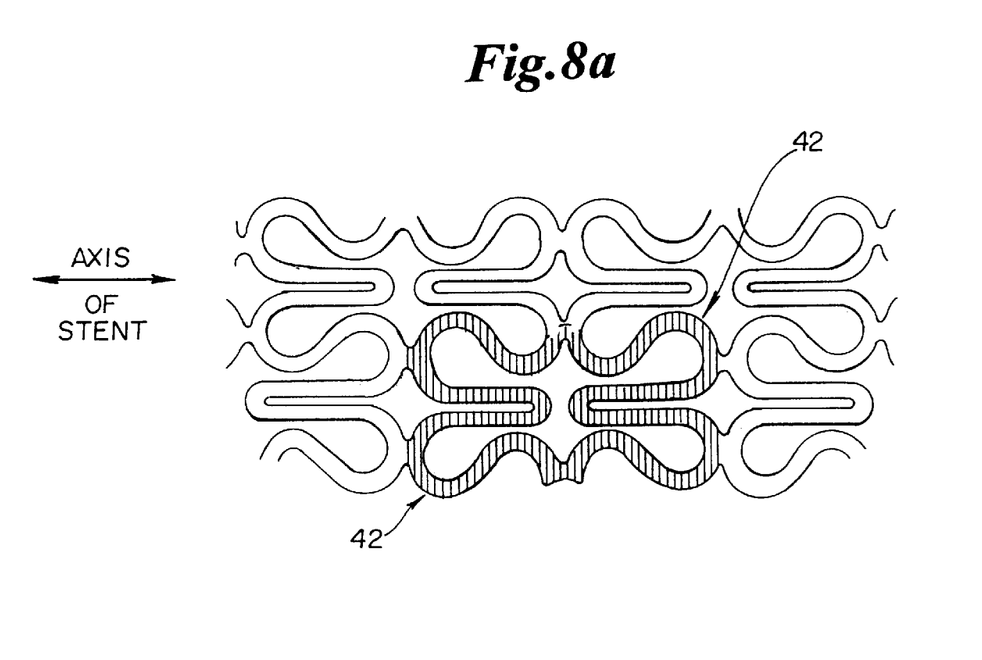
FIG. 8a is a plan view in fragment showing a variation of the cell configuration shown in FIG. 8.
Figure 9:
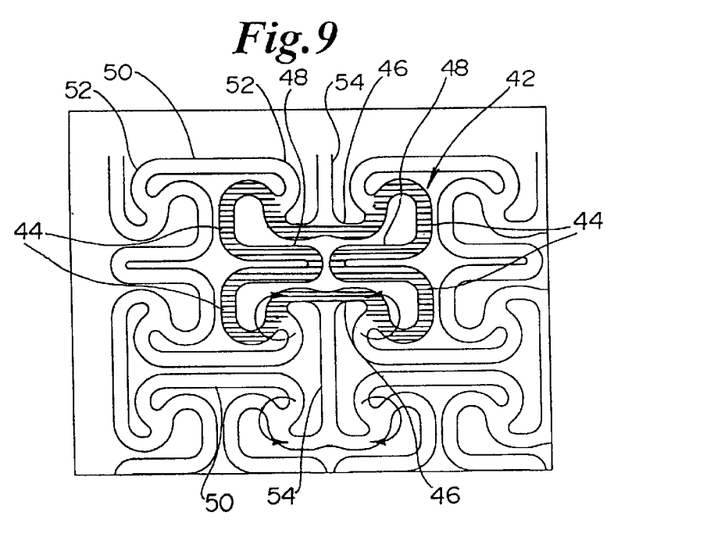
FIG. 9 is a detail view of a portion of FIG. 8, as indicated.
Figure 10:
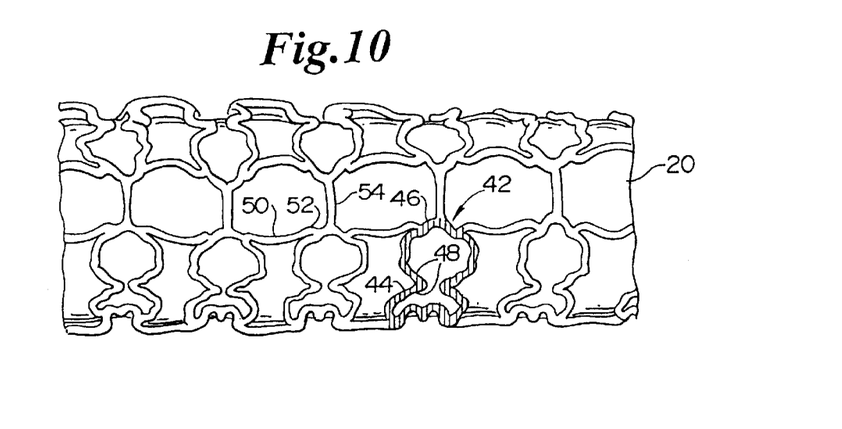
FIG. 10 is a showing of the stent of FIG. 8 expanded on a balloon.

Referring now to FIGS. 8–10, another stent embodiment of the invention is shown and generally indicated at 40. Again, as seen in FIGS. 8 and 9, expansion cells 42 (example darkened for clarity) have relatively wide end portions 44 and narrow center portions 46. The end portions include inwardly extending loop portions 48. Cells 42 are arranged end to end in longitudinal rows as in the preceding embodiments. Adjacent end portions 44 are interconnected by pairs of longitudinal support member segments 50 which have curved end portions 52. Circumferentially extending segments 54 extend between rows of cells 42 to interconnect the narrow center portions 46 of the cells. FIG. 8a shows a variation in shape for cells 42.

Upon radial expansion of the stent upon a balloon 20, the configuration changes to that shown in FIG. 10. The arrows show the direction of force of deformation upon expansion.

Figure 11:
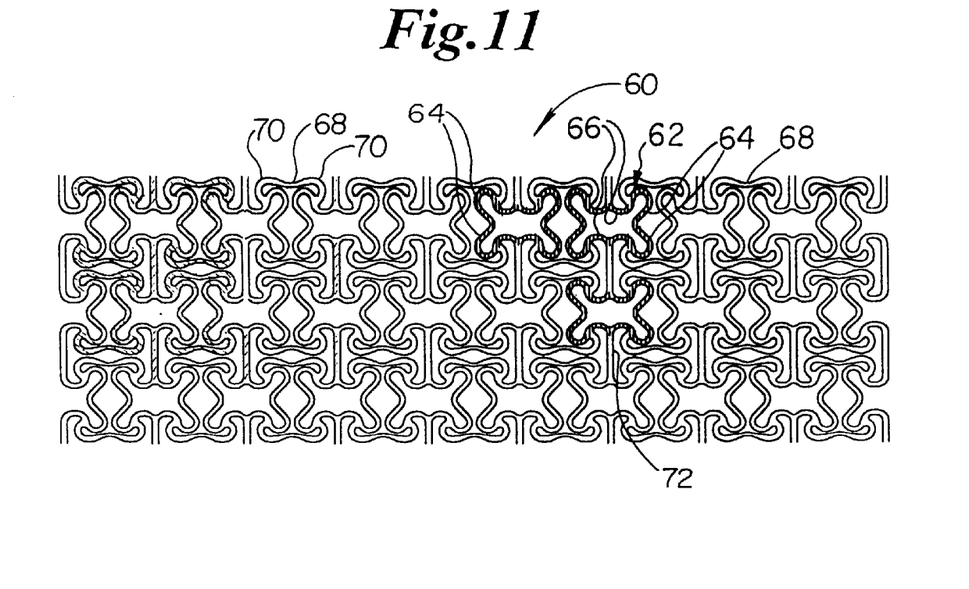
FIG. 11 is a flat plan similar to FIGS. 1, 5, and 8 showing yet another stent embodiment in the unexpanded condition.
Figure 12:
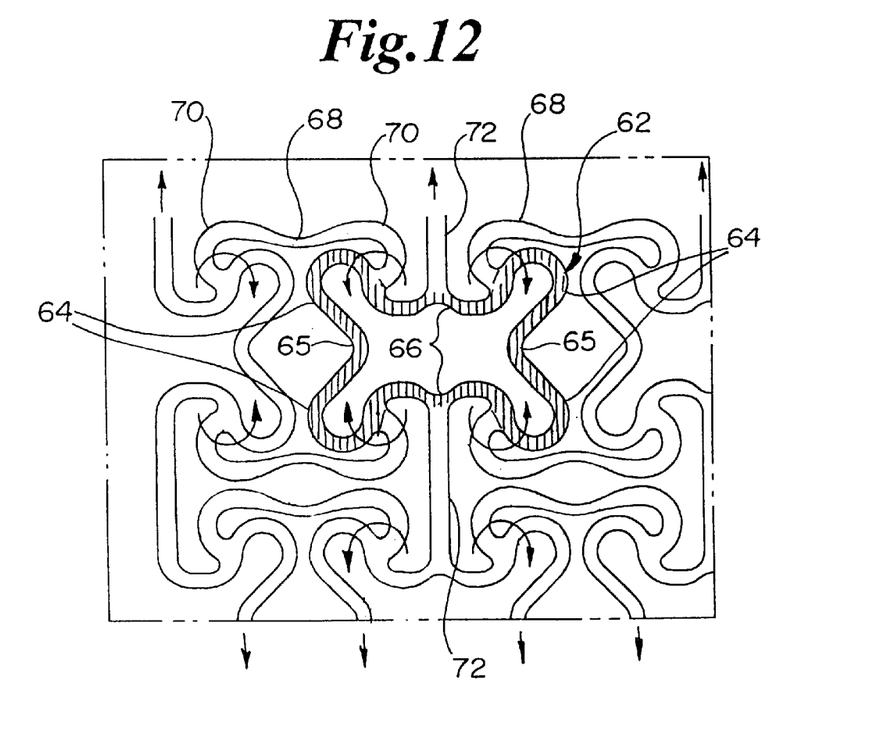
FIG. 12 is a detail view of a portion of FIG. 11, as indicated.

Referring now to FIGS. 11 and 12, still another embodiment of a stent 60 is shown. Again, as shown in FIGS. 11 and 12, expansion cells 62 (example darkened for clarity) have relatively wide end portions 64 having a slight inward bend 65 to them and narrow center portions 66. Cells 62 are arranged end to end in longitudinal rows as in the preceding embodiments. Adjacent end portions 64 are interconnected by pairs of longitudinal support member segments 68 which have curved end portions 70. Circumferentially extending segments 72 extend between rows of cells 62 to interconnect the narrow center portions 66 of the cells.

Figure 13:
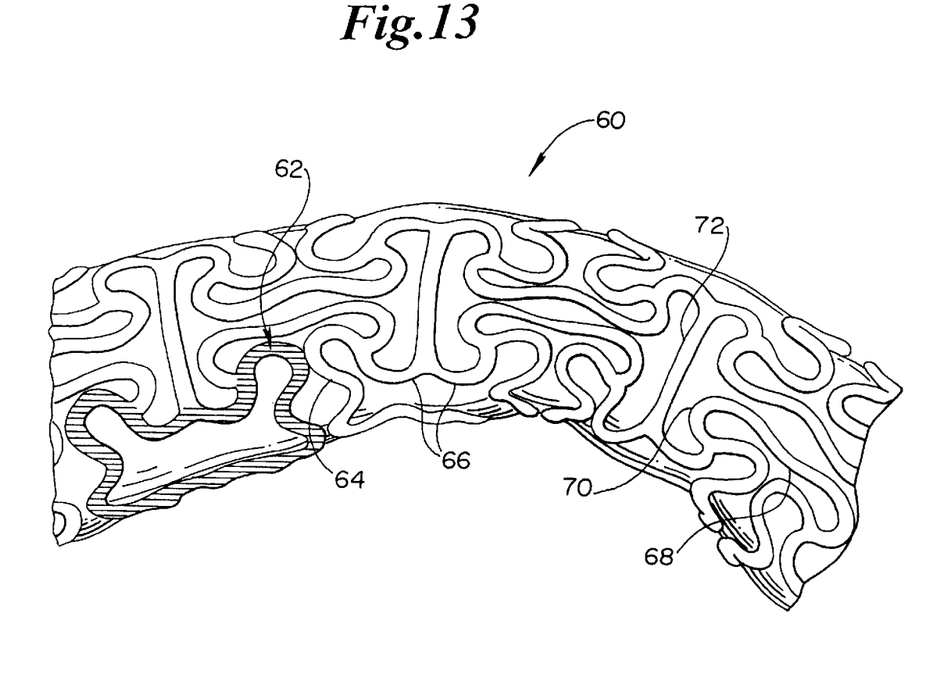
FIG. 13 is a view of the stent of FIG. 11 on an unexpanded balloon demonstrating its flexibility in the unexpanded condition.

Reference to FIG. 13 will show the inherent flexibility of the stents of this invention.

Figure 14:
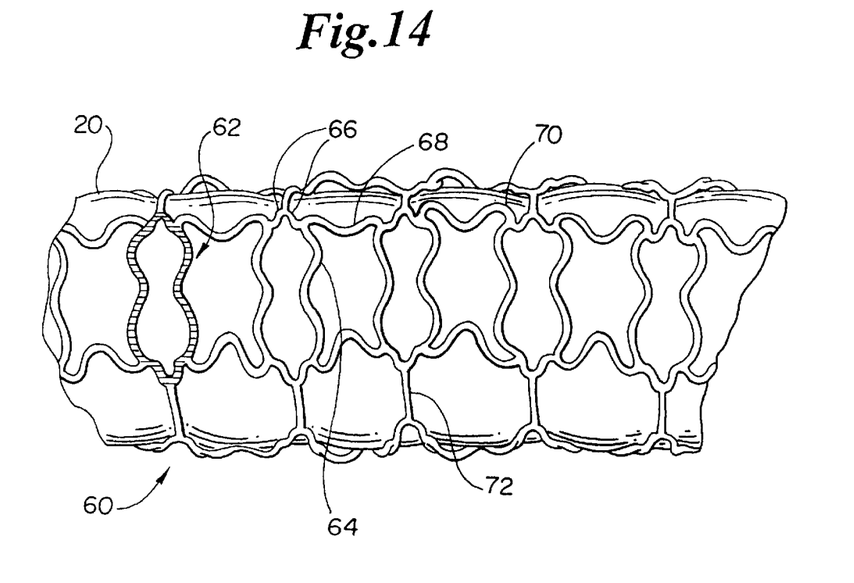
FIG. 14 is a showing of the stent of FIG. 11 expanded on a balloon.

Upon radial expansion of the stent upon a balloon 20, the configuration changes to that shown in FIG. 14.

Figure 15:
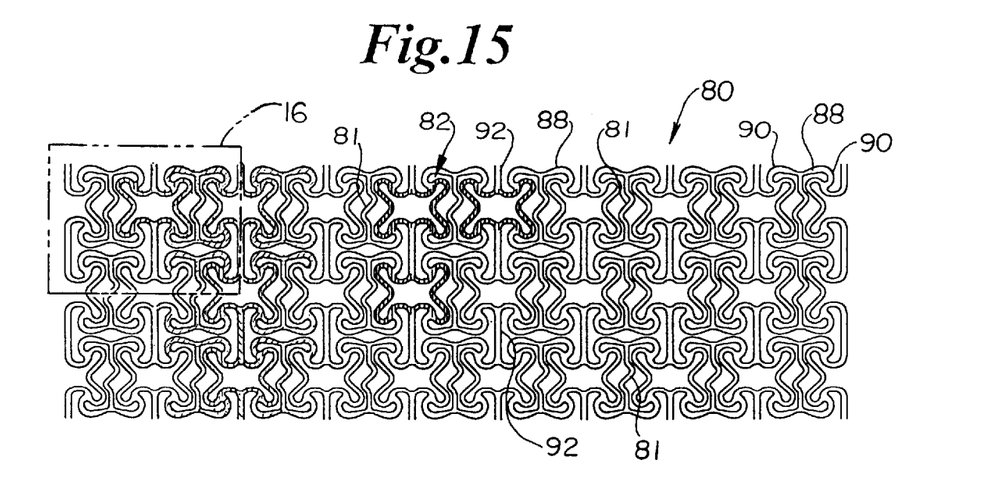
FIG. 15 is a flat plan similar to FIGS. 1, 5, 8, and 11 showing yet another stent embodiment in the unexpanded condition.
Figure 16:
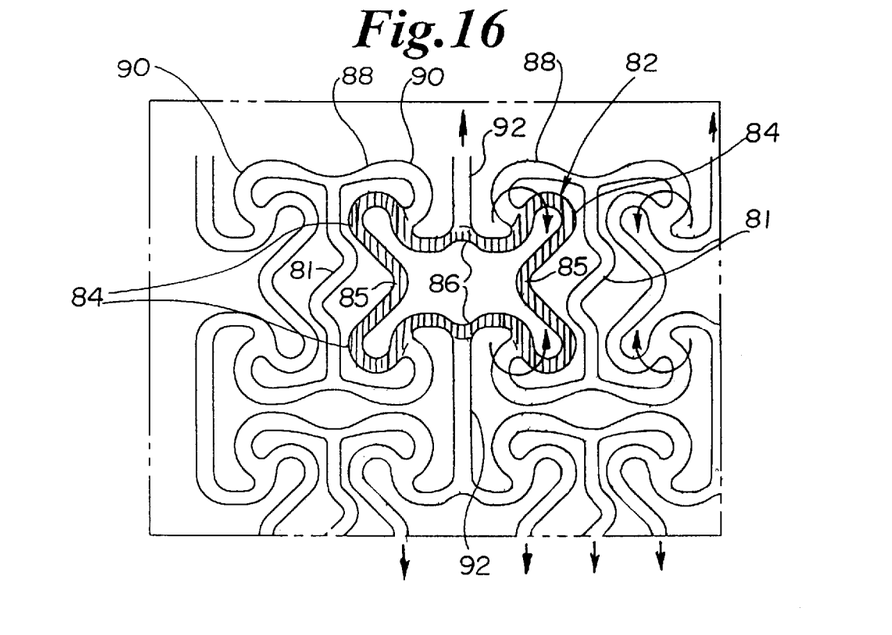
FIG. 16 is a detail view of a portion of FIG. 15, as indicated.

Referring now to FIGS. 15 and 16, yet another embodiment of a stent 80 is shown in a configuration quite similar to that of FIGS. 11–14 but with an added circumferentially extending structural element 81. Again, as best seen in FIG. 16, expansion cells 82 (examples darkened for clarity) have relatively wide end portions 84 having a slight inward bend 85 to them and narrow center portions 86. Cells 82 are arranged end to end in longitudinal rows as in the preceding embodiments. Adjacent end portions 84 are interconnected by pairs of longitudinal support member segments 88 which have curved end portions 90. Circumferentially extending segments 92 extend between rows of cells 82 to interconnect the narrow center portions 86 of the cells. Circumferentially extending segments 81 interconnect pairs of support member segments 88.

Figure 17:
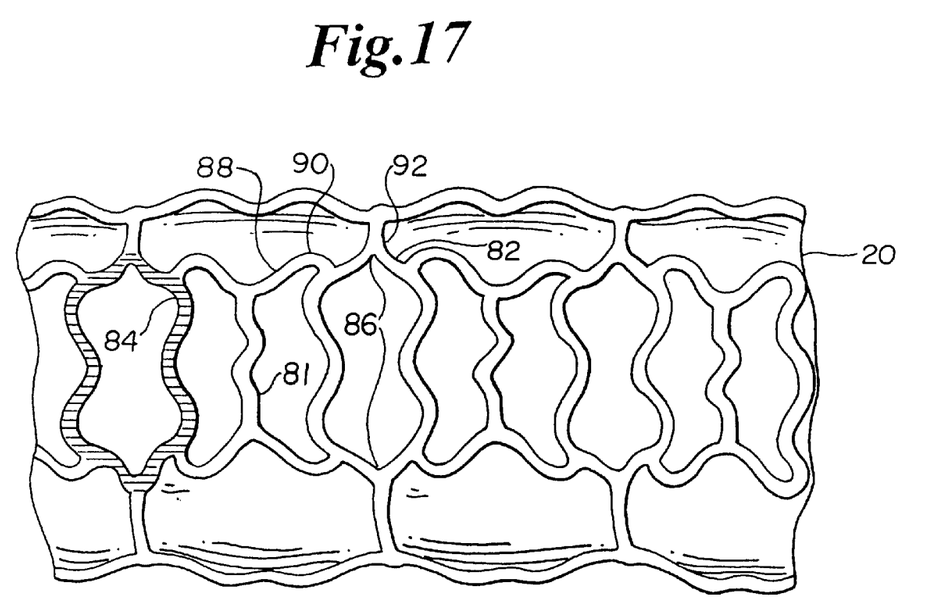
FIG. 17 is a showing of the stent of FIG. 15 expanded on a balloon.

Upon radial expansion of the stent on a balloon 20, the configuration changes to that shown in FIG. 17.

Figure 18:
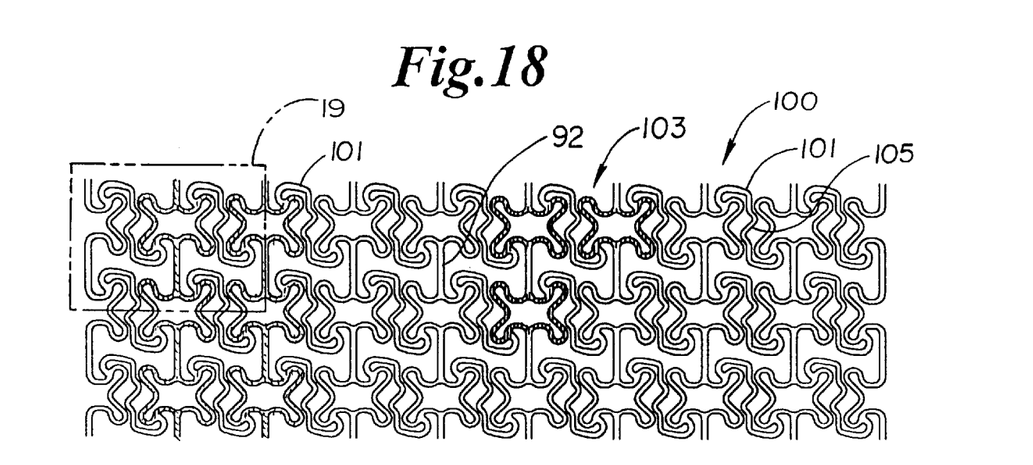
FIG. 18 is a flat plan similar to FIGS. 1, 5, 8, 11 and 15 showing still another stent embodiment in the unexpanded condition.
Figure 19:
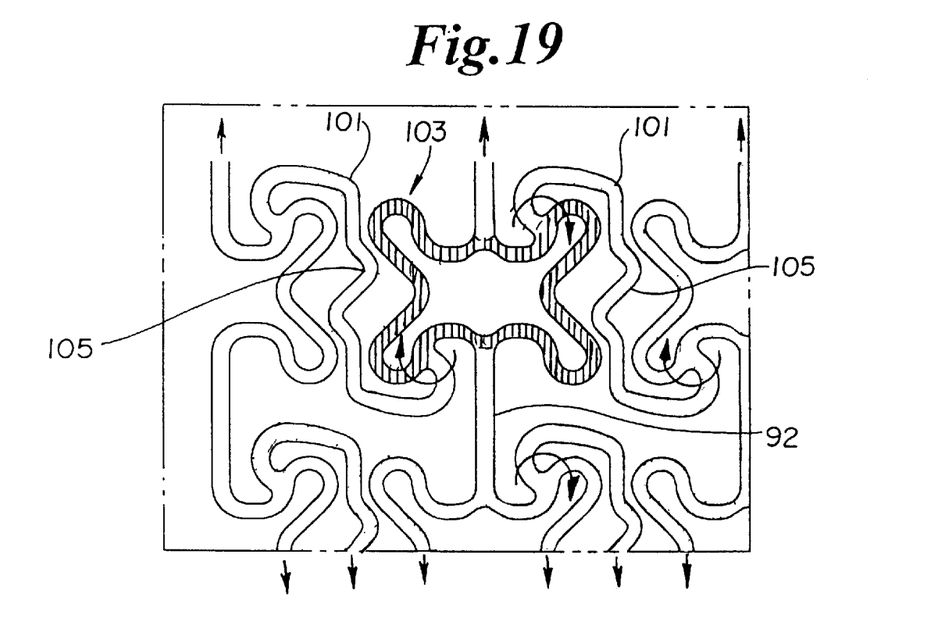
FIG. 19 is a detail view of a portion of FIG. 18, as indicated.

Referring now to FIGS. 18 and 19, still another embodiment of a stent configuration 100 is shown. As before this embodiment is similar to that of FIGS. 11–12 except that the circumferentially extending segments 101 are arranged differently than those identified in FIGS. 11–12 as 72. In this embodiment the circumferentially extending members 101 extend between the adjacent ends of adjacent cells 103 (examples darkened for clarity) to interconnect the top of one end to the bottom of the adjacent end and the members 101 have a slight curve or bend 105 in their length. The other members are all similarly numbered as in the preceding Figures.

Figure 22:
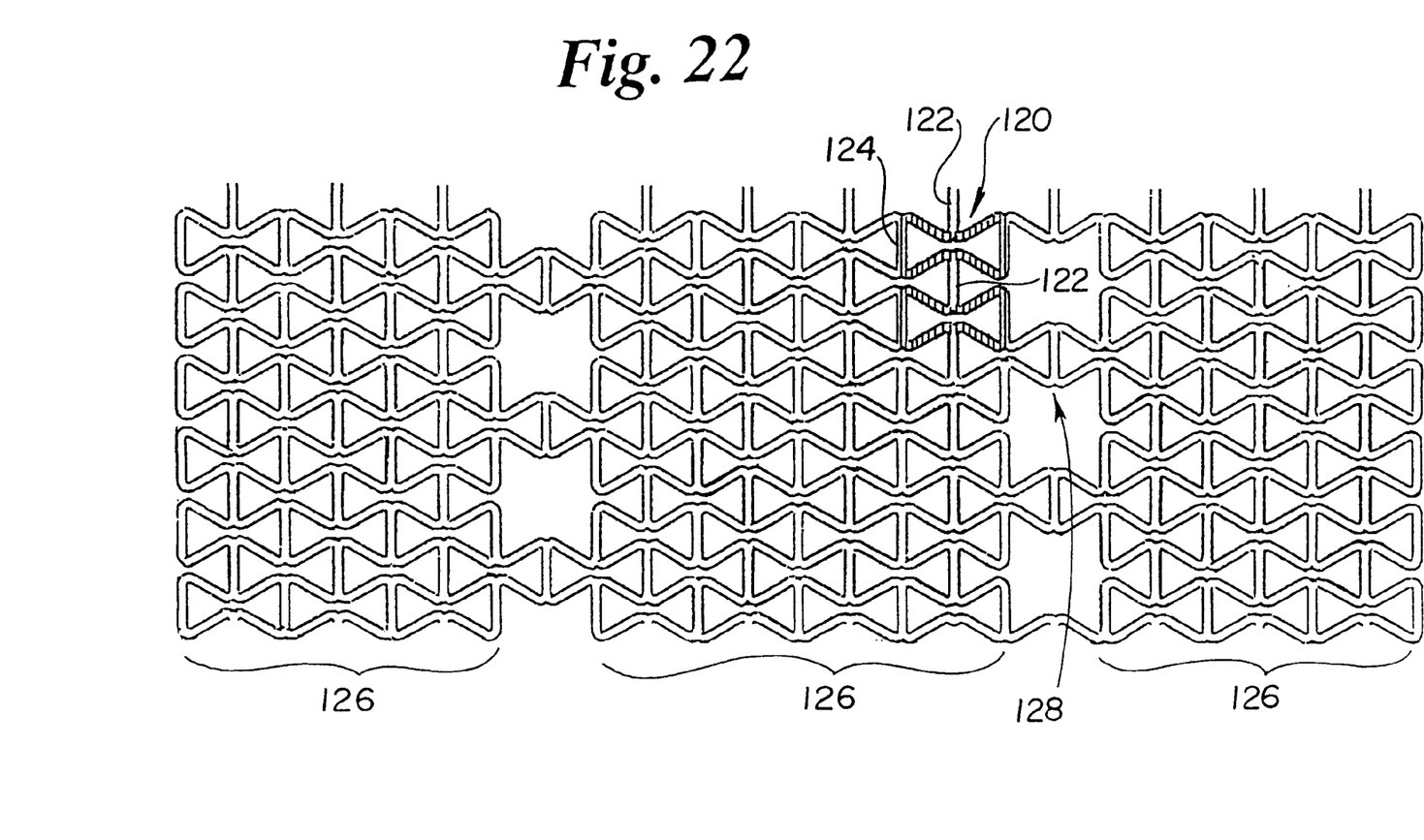
FIG. 22 is a flat plan view of another embodiment of the invention.

FIG. 22 shows yet another embodiment of a stent comprised of cells 120 having interconnecting circumferential extending members 122. The cells have common sides or end members 124 and are arranged in groups to form bands 126 which are interconnected by joined cells 128.

While this invention may be embodied in many different forms, there are described in detail herein specific preferred embodiments of the invention. This description is an exemplification of the principles of the invention and is not intended to limit the invention to the particular embodiments illustrated.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. A stent of generally cylindrical shape and having a longitudinal axis comprising interconnected regularly arranged curvilinear bodies, the curvilinear bodies providing individual closed expansion cells, the cells having relatively wide end portions joined by a relatively narrow center portion, the end portions of a cell longitudinally displaced from one another, the cells being arranged end portion to end portion longitudinally with respect to the longitudinal axis of the stent, the curvilinear bodies being interconnected by one or more interconnecting elements which extend from one curvilinear body to another.

2. The stent of claim 1 in an expanded state.

3. The stent of claim 1 in the unexpanded state.

4. The stent of claim 1 wherein the curvilinear bodies are also arranged in longitudinal rows with respect to the longitudinal axis of the stent.

5. The stent of claim 4 wherein the longitudinal rows of curvilinear bodies are substantially parallel.

6. The stent of claim 4 wherein the rows of cells are substantially parallel and the cells in the rows are in alignment circumferentially.

7. The stent of claim 1 wherein cells which are longitudinally adjacent one another are interconnected by interconnecting elements which extend from like sides of the adjacent cells.

8. The stent of claim 1 wherein cells which are longitudinally adjacent one another are interconnected by interconnecting elements which extend from opposite sides of the adjacent cells.

9. The stent of claim 1 wherein the interconnecting elements are rotationally interconnected to the curvilinear bodies.

10. A stent of generally cylindrical shape and having a longitudinal axis comprising interconnected separate regularly arranged curvilinear bodies, the curvilinear bodies providing individual closed expansion cells, the cells having relatively wide end portions joined by a relatively narrow center portion and being arranged end to end longitudinally with respect to the longitudinal axis of the stent, the curvilinear bodies being interconnected by one or more rotational elements which extend from one curvilinear body to another, each rotational element having a first end and a second end, which rotate on expansion of the stent.

11. The stent of claim 10 including rotational elements which interconnect adjacent curvilinear bodies which are longitudinally displaced from one another and including rotational elements which interconnect adjacent curvilinear bodies which are displaced circumferentially relative to one another.

12. A stent of generally cylindrical shape and having a longitudinal axis comprising:

a plurality of curvilinear bodies providing closed expansion cells, the cells being formed of relatively wide end portions and narrow center portions and being arranged end to end longitudinally along the longitudinal axis of the stent;

rotational interconnecting elements interconnecting the end portions of adjacent cells, each rotational element having a first end and a second end, which rotate on expansion of the stent; and circumferentially extending members which extend between the narrow center portions of cells which are circumferentially adjacent one another.

13. The stent of claim 12 wherein each end portion of the closed expansion cells has a top and a bottom, the rotational elements extending between longitudinally adjacent cell end portions interconnecting the top of one cell end to the bottom of another.

14. The stent of claim 13 wherein the bodies are also arranged end to end in substantially parallel longitudinal rows.

15. A stent comprising:

a plurality of interconnected cells including a first cell and a second cell longitudinally displaced from the first cell, an element extending between the first cell and the second cell, the element having a first end and a second end longitudinally and circumferentially offset from the first end, the element having at least one turn.

16. The stent of claim 15 wherein the cells are arranged in circumferential rows, the first cell and the second cell being in rows which are adjacent one another.

17. The stent of claim 15 wherein the cells are arranged in circumferential rows, a plurality of elements extending between rows which are adjacent one another, the elements having circumferential and longitudinal components.

18. An unexpanded stent comprising a plurality of cells and a plurality of intercellular elements having turns, the intercellular elements extending between the cells, the intercellular elements having first ends and second ends which are longitudinally and circumferentially displaced from the first ends.

19. The unexpanded stent of claim 18 comprising intercellular elements which have a plurality of turns.

* * * * *